United States Patent [19]

Bergman

[11] Patent Number: 5,461,027
[45] Date of Patent: Oct. 24, 1995

[54] MICROENCAPSULATED PENDIMETHALIN AND METHOD OF MAKING AND USING SAME

[75] Inventor: Elliot Bergman, Valdosta, Ga.

[73] Assignee: Griffin Corporation, Valdosta, Ga.

[21] Appl. No.: 144,891

[22] Filed: Oct. 27, 1993

Related U.S. Application Data

[63] Continuation-in-part of Ser. No. 974,674, Nov. 12, 1992, Pat. No. 5,317,004, which is a continuation of Ser. No. 873,584, Apr. 21, 1992, abandoned, which is a continuation of Ser. No. 750,773, Aug. 22, 1991, abandoned, which is a continuation of Ser. No. 568,509, Dec. 10, 1990, abandoned, which is a division of Ser. No. 441,533, Nov. 27, 1989, Pat. No. 5,073,191, which is a division of Ser. No. 301,458, Jan. 24, 1989, Pat. No. 5,160,530.

[51] Int. Cl.$^6$ .......................... A01N 33/18; A01N 25/28
[52] U.S. Cl. ..................... 504/347; 71/DIG. 1
[58] Field of Search ................ 504/347; 71/DIG. 1

[56] References Cited

U.S. PATENT DOCUMENTS

| | | | |
|---|---|---|---|
| 2,800,463 | 7/1957 | Morrison | 260/29.1 |
| 3,016,308 | 1/1962 | Macaulay | 117/36.7 |
| 3,043,782 | 7/1962 | Jensen | 252/316 |
| 3,112,233 | 11/1963 | Friedman et al. | 149/4 |
| 3,159,585 | 12/1964 | Evans et al. | 252/316 |
| 3,210,208 | 10/1965 | Grass et al. | 106/148 |
| 3,257,190 | 6/1966 | Soper | 504/347 |
| 3,293,132 | 12/1966 | Stoyle et al. | 167/82 |
| 3,323,922 | 6/1967 | Durst | 99/166 |
| 3,399,069 | 8/1968 | Bridgeford | 106/164 |
| 3,429,827 | 2/1969 | Ruus | 252/316 |
| 3,455,838 | 7/1969 | Marotta et al. | 252/316 |
| 3,499,962 | 3/1970 | Wurzburg et al. | 424/35 |
| 3,501,419 | 3/1970 | Bridgeford | 260/2.5 |
| 3,501,423 | 3/1970 | Tate et al. | 260/8 |
| 3,535,423 | 10/1970 | Ordas | 424/176 |
| 3,556,765 | 1/1971 | Houston | 71/117 |

(List continued on next page.)

FOREIGN PATENT DOCUMENTS

| 1305369 | 1/1973 | United Kingdom . |
|---|---|---|
| 1371179 | 10/1974 | United Kingdom . |

OTHER PUBLICATIONS

"Applications of Spray Drying in Industry," pp. 528–531, 582–583, 611 661–668, Attachment A 1975.
Microencapsulation/Spray Drying abstract 1987.
Microencapsulation/PVA abstract 1987.
Encyclopedia Of Polymer Science And Technology, vol. 14 1972.
Goldschmiedt, PhD., "Microencapsulation," Soap/Cosmetics/Chemical Specialties for Sep. 1973, pp. 46–48.
Bakan, J. A. and Anderson, J. L., "Part III, Microencapsulation," The Theory and Practice of Industrial Pharmacy, 420 (2nd Ed. 1976), pp. 420–438.
Kondo, A. Microcapsule Processing And Technology, Chapters 1,3,4,15, 1979.
Luzzi, L. A. "Microencapsulation," Journal Of Pharmaceutical Sciences, vol. 59, No. 10, Oct. 1970.

(List continued on next page.)

Primary Examiner—S. Mark Clardy
Attorney, Agent, or Firm—Jones & Askew

[57] ABSTRACT

Pendimethalin microencapsulated in a microcapsule comprised of a water-soluble film forming polymer. The present invention also includes a method of microencapsulating low-melting agriculturally active materials, such as pendimethalin. The microencapsulation process comprises the steps of heating pendimethalin to a molten state. The molten pendimethalin is then combined with an aqueous solution of a water-soluble, film-forming polymer at a temperature sufficient to maintain the pendimethalin in its molten state. The pendimethalin is then emulsified in the aqueous solution so that the pendimethalin has a primary particle size of between approximately 0.1 and 10 microns. The resulting dispersion or emulsion is then spray dried at a temperature between approximately 50° C. and 220° C. so as to microencapsulate the pendimethalin in the polymer. Compounds for promoting the rapid solidification of the pendimethalin am also disclosed.

13 Claims, 2 Drawing Sheets

U.S. PATENT DOCUMENTS

| | | | |
|---|---|---|---|
| 3,565,818 | 2/1971 | Bayless et al. | 252/316 |
| 3,574,133 | 4/1971 | Bayless et al. | 252/316 |
| 3,577,515 | 5/1971 | Vandegaer | 424/32 |
| 3,582,495 | 6/1971 | Emrick | 252/316 |
| 3,584,113 | 6/1971 | Takebe et al. | 424/19 |
| 3,627,693 | 12/1971 | Scarpelli | 252/316 |
| 3,629,140 | 12/1971 | Bayless et al. | 252/316 |
| 3,664,963 | 5/1972 | Pasin | 252/316 |
| 3,708,573 | 1/1973 | Yoshinaga et al. | 424/23 |
| 3,748,277 | 7/1973 | Wagner | 252/316 |
| 3,778,383 | 12/1973 | Schibler et al. | 252/316 |
| 3,780,195 | 12/1973 | Balassa | 426/350 |
| 3,804,775 | 4/1974 | Shiozaki et al. | 252/316 |
| 3,875,074 | 4/1975 | Vassiliades et al. | 252/316 |
| 3,877,928 | 4/1975 | Houston et al. | 71/111 |
| 3,883,489 | 5/1975 | Matschke et al. | 260/78.5 |
| 3,900,378 | 8/1975 | Yen et al. | 204/159.14 |
| 3,920,442 | 11/1975 | Albert et al. | 71/92 |
| 3,920,742 | 11/1975 | Lutz et al. | 260/577 |
| 3,927,196 | 12/1975 | Hersh | 424/37 |
| 3,943,063 | 3/1976 | Morishita et al. | 252/316 |
| 3,959,464 | 5/1976 | DeSavigny | 424/78 |
| 3,971,852 | 7/1976 | Brenner et al. | 426/103 |
| 3,977,992 | 8/1976 | Hofacker | 252/316 |
| 3,980,463 | 9/1976 | Muramoto et al. | 71/86 |
| 3,985,840 | 10/1976 | Hofacker | 264/4 |
| 4,002,458 | 1/1977 | Hofacker | 71/27 |
| 4,011,661 | 3/1977 | Sezaki et al. | 34/12 |
| 4,016,254 | 4/1977 | Seager | 424/33 |
| 4,066,441 | 1/1978 | Lutz et al. | 71/121 |
| 4,071,617 | 1/1978 | Graves et al. | 424/78 |
| 4,082,537 | 4/1978 | Dudkowski | 71/121 |
| 4,101,582 | 7/1978 | Lutz et al. | 260/574 |
| 4,134,725 | 1/1979 | Büchel et al. | 71/DIG. 1 |
| 4,144,050 | 3/1979 | Frencsh et al. | 71/120 |
| 4,150,969 | 4/1979 | Dudkowski | 504/347 |
| 4,165,231 | 8/1979 | Lutz et al. | 71/121 |
| 4,174,960 | 11/1979 | Hendriksen | 71/121 |
| 4,185,035 | 1/1980 | Eizember et al. | 260/577 |
| 4,187,194 | 2/1980 | Wellman et al. | 252/316 |
| 4,244,836 | 1/1981 | Frensch et al. | 252/316 |
| 4,267,281 | 5/1981 | McCormick | 525/61 |
| 4,269,729 | 5/1981 | Maruyana et al. | 252/316 |
| 4,273,672 | 6/1981 | Vassiliades | 252/316 |
| 4,280,833 | 7/1981 | Beestman et al. | 71/100 |
| 4,286,020 | 8/1981 | Himel et al. | 428/407 |
| 4,335,260 | 6/1982 | Bornengo et al. | 564/406 |
| 4,344,857 | 8/1982 | Shasha et al. | 252/316 |
| 4,353,962 | 10/1982 | Himel et al. | 428/407 |
| 4,360,376 | 11/1982 | Koestler | 71/121 |
| 4,405,360 | 9/1983 | Cardarelli | 71/117 |
| 4,415,355 | 11/1983 | Cassell et al. | 71/121 |
| 4,417,916 | 11/1983 | Beestman et al. | 71/93 |
| 4,439,488 | 3/1984 | Trimnell et al. | 428/402.24 |
| 4,440,746 | 4/1984 | Maglio | 424/78 |
| 4,440,962 | 4/1984 | Pallucca | 568/933 |
| 4,450,001 | 5/1984 | Kaneko et al. | 71/118 |
| 4,464,193 | 8/1984 | Kaneko et al. | 71/83 |
| 4,482,606 | 11/1984 | Bousquet et al. | 428/402.2 |
| 4,488,896 | 12/1984 | Lamb et al. | 71/92 |
| 4,501,608 | 2/1985 | Cannon | 71/121 |
| 4,511,395 | 4/1985 | Misselbrook | 71/121 |
| 4,537,992 | 8/1985 | Pikarski et al. | 564/437 |
| 4,541,860 | 9/1985 | Civilla et al. | 71/120 |
| 4,554,155 | 11/1985 | Allan et al. | 424/22 |
| 4,563,212 | 1/1986 | Becher et al. | 71/118 |
| 4,594,096 | 6/1986 | Albrecht et al. | 71/93 |
| 4,622,315 | 11/1986 | Dureja et al. | 514/70 |
| 4,640,709 | 2/1987 | Beestman | 71/100 |
| 4,657,582 | 4/1987 | Huber | 71/121 |
| 4,670,250 | 6/1987 | Baker | 424/419 |
| 4,690,786 | 9/1987 | Ninomiya et al. | 264/4.6 |
| 4,749,812 | 6/1988 | Takematsu et al. | 71/118 |
| 4,755,397 | 7/1988 | Eden et al. | 427/43.3 |
| 4,845,888 | 6/1989 | Lahalih et al. | 47/9 |
| 4,874,425 | 10/1989 | Kimpara et al. | 71/121 |
| 4,875,925 | 10/1989 | Hewett et al. | 71/94 |
| 4,882,166 | 11/1989 | Graham et al. | 424/462 |
| 4,936,901 | 6/1990 | Surgant, Sr. et al. | 71/92 |
| 4,985,064 | 1/1991 | Redlich et al. | 71/90 |
| 5,022,182 | 6/1991 | Anderson | 47/48.5 |
| 5,049,182 | 9/1991 | Scher et al. | 71/93 |
| 5,074,905 | 12/1991 | Frisch et al. | 71/120 |
| 5,078,781 | 1/1992 | Finch, Jr. | 71/94 |
| 5,087,456 | 2/1992 | Meinard et al. | 424/501 |

OTHER PUBLICATIONS

Tsunemitsu, K., and Shohata, H., "Useful Properties and Industrial Uses of Polyvinyl Alcohol as a Water–Soluble Polymer," S.C.I. Monograph No. 30, pp. 104–129 1968.

Hackel, E., "Industrial Methods for the Preparation of Polyvinyl Alcohol," S.C.I. Monograph No. 30, pp. 1–15 1965.

"Microencapsulation By Spray–Drying Process," (Attachment B), Chapter 15, pp. 154–165 1979.

Chemical Abstracts vol. 84: 79741h (1976).

Chemical Abstracts vol. 83, col. 148614n (1975).

83 Chemical Abstracts, p. 276, col. 168481v (1975).

80 Chemical Abstracts, p. 42, col. 84172v (1974).

78 Chemical Abstracts, p. 262, col. 33916s (1973).

Chemical Abstracts vol. 77, p. 113, col. 128592b (1972).

Chemical Abstracts vol. 76, p. 41, col. 26106h (1972).

Chemical Abstracts, p. 2216, col. 22766k (1968).

Chemical Abstracts vol. 66, p. 2849, col. 29562h (1967).

Chemical Abstracts vol. 57, col. 8693a (1962).

Chemical Abstracts vol. 56, col. 8878a (1962).

Chemical Abstracts, vol. 55, col. 26551b (1962).

Chemical Abstracts, vol. 37, col. $4536^1$ (1943).

Chemical Abstracts vol. 91, col. 162997m (1979).

Chemical Abstracts, p. 701, col. 83549(d) (1988).

chemical Abstracts 83 (148615p) (1975).

World Patent Search 1980.

Calif. 106: 183056x. Dumas, J. P., et al. "Phase Transformations in Emulsions. Part II. Polymorphison . . . " *J. Dispersion Sci. & Tech.* 1987, 8(1), 29–54.

MICROENCAPSULATED PENDIMETHALIN AND METHOD OF MAKING AND USING SAME

CROSS-REFERENCE TO RELATED APPLICATIONS

The present application is a continuation-in-part of application Ser. No. 974,674 filed Nov. 12, 1992, now U.S. Pat. No. 5,317,004 which is a continuation of application Ser. No. 873,584 filed Apr. 21, 1992, now abandoned, which is a continuation of application Ser. No. 750,773 filed Aug. 22, 1991, now abandoned, which is a continuation of application Ser. No. 568,509 filed Dec. 10, 1990, now abandoned, which is a division of application Ser. No. 441,533 filed Nov. 27, 1989, now U.S. Pat. No. 5,073,191, which is a division of application Ser. No. 301,458 filed Jan. 24, 1989, now U.S. Pat. No. 5,160,530.

FIELD OF THE INVENTION

The present invention relates generally to microencapsulated agriculturally active materials, such as pesticides, herbicides and the like, and to a process for producing said microencapsulated materials. More particularly, the present invention relates to a microencapsulated form of pendimethalin and to a process for making and using the same. The present invention also relates to crystallization initiators and stabilizers for said microencapsulated pendimethalin.

BACKGROUND OF THE INVENTION

Agriculturally active materials, such as pesticides, herbicides and the like, are widely used throughout the agricultural industry. For convenience in packaging and handling, such agriculturally active materials are typically produced in the form of a dry solid, such as a powder, which can be readily mixed with water. The aqueous solution or dispersion of the active material is then typically applied to an area to be treated by spraying.

In order to produce aqueous solutions or dispersions suitable for application by spraying, the agriculturally active material must be in a form which can be readily incorporated with water. The agriculturally active material by itself, however, is usually insoluble in water or has an unacceptably low water solubility. Therefore, it is usually necessary to treat the agriculturally active material in some manner to enhance its combinability with water.

One such method of treating agriculturally active materials is microencapsulation. For example, U.S. Pat. No. 4,280,833 discloses a process for microencapsulating water-immiscible materials, such as herbicides, and, specifically, trifluralin. The microencapsulation process involves an aqueous phase containing an emulsifier and an organic phase. The organic phase consists of a water-immiscible material, such as trifluralin, and polymethylene polyphenylisocyanate. The organic phase is added to the aqueous phase with agitation to form a dispersion of small droplets of the organic phase within the aqueous phase. Thereafter, a polyfunctional amine is added to the dispersion. The polyfunctional amine reacts with the isocyanate to form a capsular polyurea shell about the herbicide droplet. This type of microencapsulation process is termed interfacial polycondensation. Other patents which involve microencapsulation by polycondensation processes include U.S. Pat. Nos. 4,360,376; 4,417,916; 4,563,212; 3,429,827; 3,577,515; 3,959,464 and 4,640,709.

Another process used to microencapsulate active materials is spray drying. U.S. Pat. No. 4,244,836 relates to a microencapsulation process using spray drying. In that process, a liquid, water-insoluble phase is dispersed in an aqueous phase. The liquid, water-insoluble phase can be materials such as plant protecting agents. The aqueous phase is a polyvinyl alcohol solution. The water-insoluble phase is dispersed in the aqueous phase using a stirrer or a homogenization device so as to produce droplets of the water-insoluble phase of from 1 to 50 microns in diameter within the aqueous phase. The dispersion is then atomized into a stream of heated air (spray dried). The spray drying dehydrates the aqueous dispersion and produces a dry powdery microcapsular product. Other patents which utilize a spray drying technique for microencapsulation include U.S. Pat. Nos. 4,286,020; 4,353,962 and 4,690,786.

While various microencapsulation processes are known for various active materials, the microencapsulation of pendimethalin is not known. Furthermore, the microencapsulation of many agricultural herbicides requires the use of an organic solvent, such as xylene, for the herbicide in order to microencapsulate the herbicide. When the herbicide is applied to soil, the solvent for the herbicide is applied to the soil as well. It is obviously undesirable to apply organic solvents to agricultural field as many pollution problems will result therefrom.

SUMMARY OF THE INVENTION

Generally speaking, the present invention relates to herbicidal compositions in a desired form having improved physical properties and to a process for microencapsulating said herbicidal compositions. More particularly, the present invention includes a process of microencapsulating pendimethalin. The microencapsulation process comprises the steps of heating pendimethalin to a molten state. The molten pendimethalin is then combined with an aqueous solution of a water-soluble, film-forming polymer at a temperature sufficient to maintain the pendimethalin in its molten state. The pendimethalin is then emulsified in the aqueous solution so that the active material has a primary particle size of between approximately 1 and 12 microns. The resulting emulsion is then spray dried at a temperature between approximately 50° C. and 220° C. so as to microencapsulate the pendimethalin in the polymer. In another embodiment of the present invention, the pendimethalin is combined with a crystallization initiating compound prior to encapsulation.

Another aspect of the invention is providing a pesticidal composition comprising pendimethalin microencapsulated in a microcapsule of a water-soluble, film-forming polymer. In another embodiment of the present invention, the pendimethalin is combined with a crystallization initiating compound. This microencapsulated form of pendimethalin has improved physical properties compared to prior art compositions. In particular, the microencapsulated pendimethalin of the present invention has improved properties of dispersibility, suspensibility and storage stability.

Accordingly, it is an object of the present invention to provide improved agriculturally active compositions containing pendimethalin.

Another object of the present invention is to provide an improved method of microencapsulating pendimethalin.

Yet another object of the present invention is to provide pendimethalin in a form having improved dispersibility.

Still another object of the present invention is to provide pendimethalin in a form having improved suspensibility.

Another object of the present invention is to provide pendimethalin in a form having improved storage stability.

A further object of the present invention is to provide pendimethalin in a form which is capable of being cycled from a solid form, through the melting point of pendimethalin and back to a solid form.

Still another object of the present invention is to provide pendimethalin in a form which is substantially dry and free-flowing.

Another object of the present invention is to provide a form of pendimethalin which has improved properties of rapid solidification or crystallization.

These and other objects, features and advantages of the present invention will become apparent after a review of the following detailed description of the disclosed embodiments and the appended claims.

BRIEF DESCRIPTION OF THE DRAWINGS

FIG. 1 is simplified graphic illustration of the dehydration of an emulsion droplet.

FIG. 2 is a simplified graphic illustration of the emulsion droplet of FIG. 1 after drying showing encapsulated pendimethalin.

DETAILED DESCRIPTION OF THE DISCLOSED EMBODIMENTS

The invention relates to microencapsulation of agriculturally active materials, such as herbicides, insecticides, fungicides, nematicides, miticides and plant growth regulators. The specific agriculturally active material useful in the present invention is pendimethalin. Pendimethalin has the chemical formula N-(1-ethylpropyl)-3,4-dimethyl-2,6-dinitrobenzenamine.

One disclosed embodiment of the present invention involves a process for the microencapsulation of pendimethalin. The microencapsulation process is performed by first providing an aqueous solution of a water-soluble, film-forming polymer. Pendimethalin is then heated to a temperature above its melting point so that the normally solid material becomes liquid. The molten pendimethalin is then combined with the aqueous phase. The temperature of the aqueous phase must be such that when the molten pendimethalin is added thereto, the molten pendimethalin remains molten. The pendimethalin is then emulsified in the aqueous phase by vigorous agitation or mixing with appropriate apparatus well known in the art, such as high shear mixers or homogenizers. The objective of this emulsifying step is to convert the molten pendimethalin into a plurality of tiny liquid droplets uniformly dispersed in the aqueous phase. Accordingly, the dispersing or emulsifying step should be conducted so as to provide droplets of liquid pendimethalin having a primary particle size of between approximately 1 and 12 microns; preferably, between approximately 2 and 4 microns.

Figure 1:
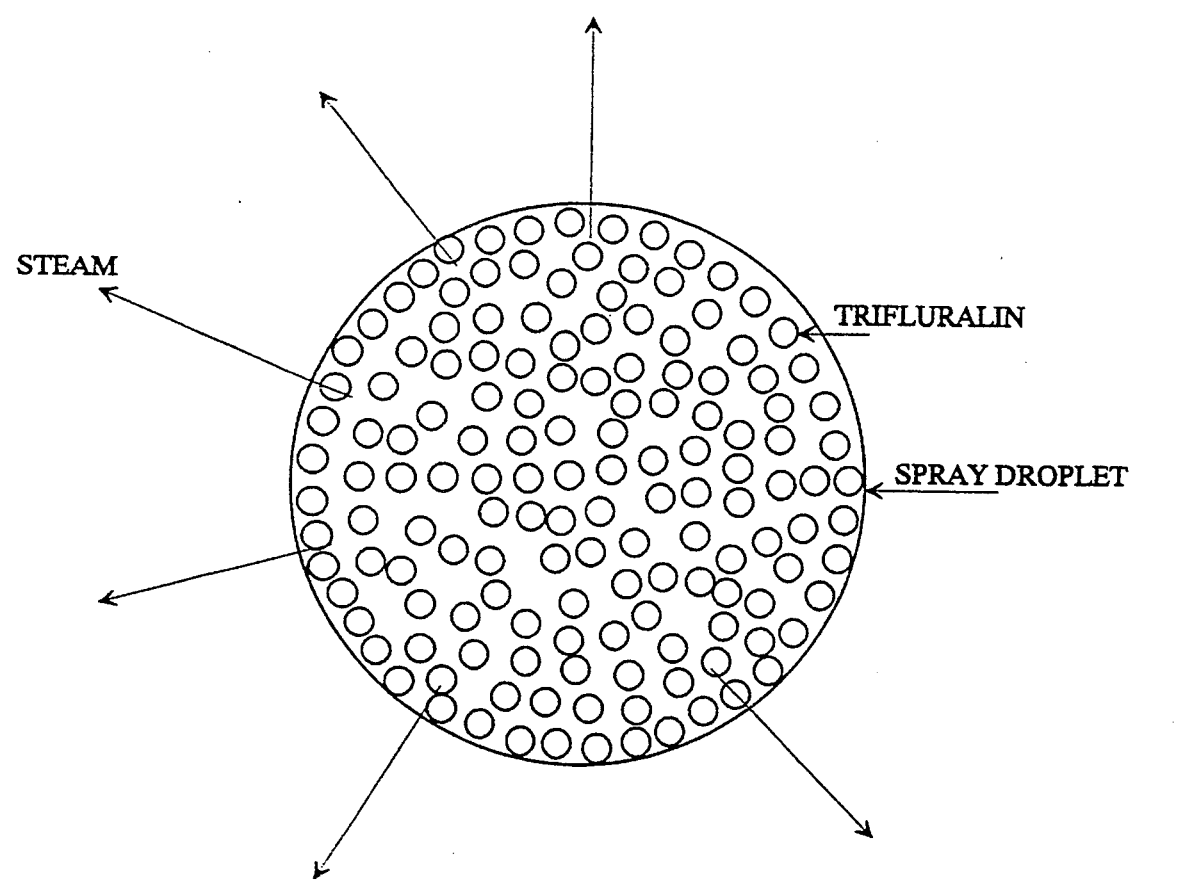

The resulting emulsion of the active material in the aqueous phase is then spray dried using conventional spray drying equipment which is well known to those skilled in the art. The purpose of spray drying the emulsion is to dehydrate it (FIG. 1) and thereby form a capsule wall of the film-forming polymer around the droplets of pendimethalin. In order to accomplish this dehydration step, the emulsion is spray dried at a temperature between approximately 50° C. and 220° C. In terms of conventional spray drying equipment, the spray drying should be conducted using an air inlet temperature of between approximately 80° C. and 250° C.; preferably, between approximately 180° C. and 250° C. An air outlet temperature of between approximately 80° C. and 110° C. is used. The spray dryer preferably uses hydraulic nozzle atomization. The atomization nozzle is preferably operated at a pressure of between approximately 500 and 1,100 p.s.i.

Figure 2:
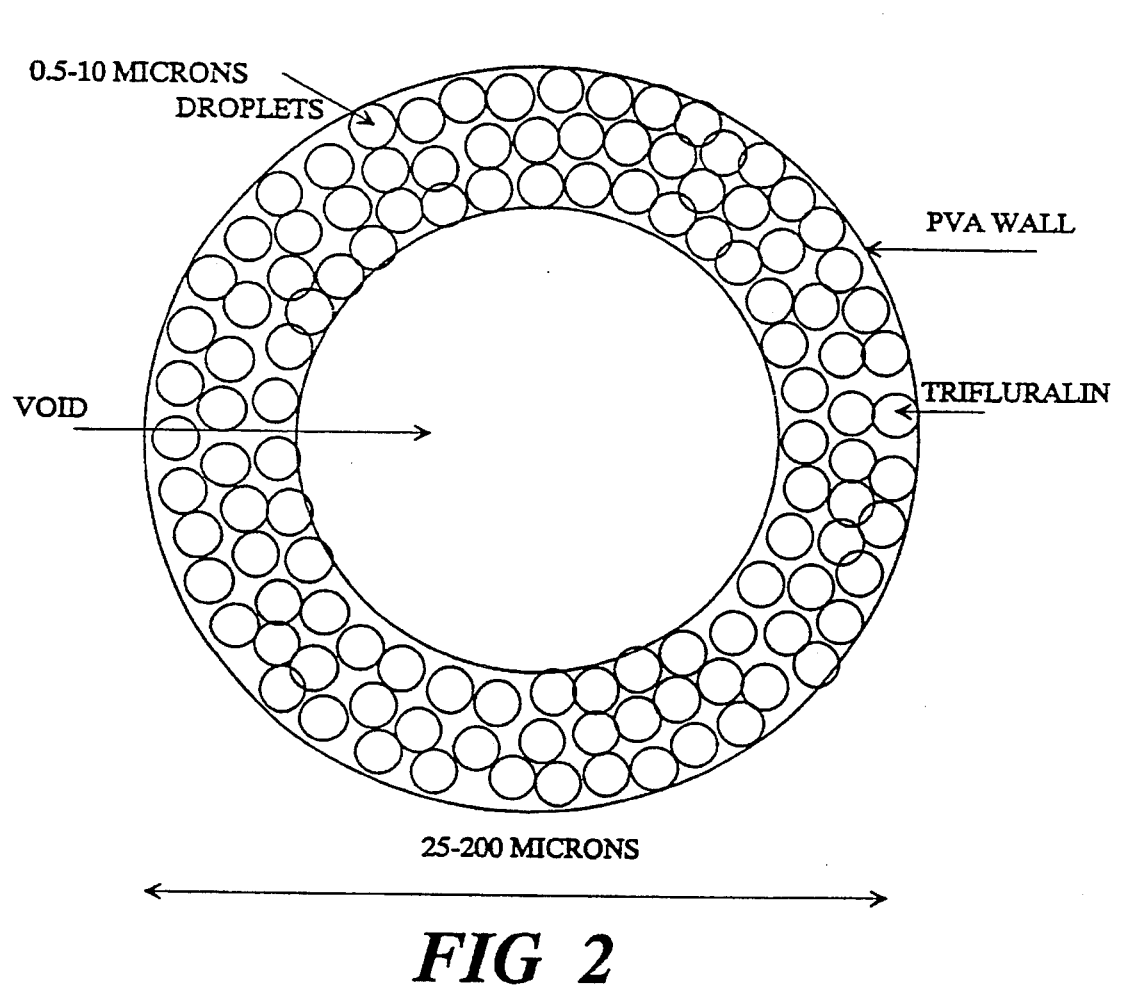

The spray drying process produces dry, free-flowing product containing the pendimethalin. The free-flowing product containing the pendimethalin formed by the spray drying process will generally have a particle size of between approximately 10 and 500 microns. (FIG. 2).

The amount of active material which is added to the aqueous phase is not especially critical but is generally between approximately 5% and 75% by weight; preferably, between approximately 20% and 30% by weight, and especially approximately 25% by weight. The aqueous phase comprises a solution of between approximately 1% and 50% by weight; preferably, between approximately 5% and 20% by weight, of a water-soluble, film-forming polymer. When the foregoing concentrations of pendimethalin and film-forming polymer are used, the pendimethalin represents between approximately 60% and 75 % by weight; preferably approximately 70% by weight, of the dried, finished microencapsulated product.

The water-soluble, film-forming polymers which can be used in connection with the present invention are not especially critical. Any suitable water-soluble, film-forming polymer can be used. Examples of water-soluble, film-forming polymers which can be used are: polyvinyl alcohol, polyvinylpyrrolidone, starches, modified starches, alginates, hydroxyalkylcellulose, hydroxyalkylcellulose derivatives, poly (acrylic acid), and homologs and salts thereof, polyacrylamide, natural gums, such as gum arabic, dextrins and proteins, such as gelatin and casein. A particularly useful water-soluble, film-forming polymer is polyvinyl alcohol having a degree of hydrolysis of between approximately 75% and 99%; preferably, between approximately 85% and 90%, and a molecular weight of between approximately 10,000 and 100,000; preferably, between approximately 10,000 and 30,000.

Additives to modify the nature of the microcapsule polymer wall can also be added to the aqueous phase. Examples of such additives are plasticizers, wetting agents and anticaking agents.

It is an essential aspect of the present invention that the pendimethalin contained in the microcapsule must predominately be in a solid or crystallized state, as opposed to being in a liquid state. By merely permitting the microcapsules to return to ambient or room temperature (approximately 20° C.), the conversion of the pendimethalin from the molten to the solid state will occur slowly. One method of improving the conversion of pendimethalin from the solid to the liquid state is to cool the spray dried microcapsules in a fluid bed at a temperature of between approximately 15° C. and 27° C. Fluid beds are well known in the art and the particular design of the fluid bed is not critical to the present invention.

As a part of the present invention, it has been discovered that the degree of conversion of the pendimethalin from liquid to solid can be increased by the use of crystallization initiators or stabilizers. Materials which have been found to help promote the solidification or crystallization of pendimethalin include: organic acids and salts, such as Benzoic Acid, Sodium Benzoate, Salicylic Acid; 3-Hydroxybenzoic Acid and 4-Hydroxybenzoic Acid; dinitroanilines, such as 3,5-dinitro-$N^4$, $N^4$-dipropylsulfanilamide and 2-dipropylamino-3,5-dinitrobenzotrifluroride; and surfactants, such as Diethylene glycol monostearate, Polyethylene glycol 400 monostearate, Sorbitan monostearate, Sorbitan monooleate, Sorbitan trioleate, Polyoxyethylene (20) sorbitan monolaurate, Polyoxyethylene (20) sorbitan monooleate, Polyoxyethylene (20) sorbitan monostearate, Polyoxyethylene (20) sorbitan trioleate, Sodium or Calcium dodecylbenzene sulfonate, Tetrasodium N-(1,2-dicarboxyethyl)-N-octadecyl-sulfosuccinamate, Dioctyl ester of sodium sulfosuccinic acid, Sodium N-Methyl-N-oleoyl taurate, Sorbitan monolaurate, Tetramethyl decyndiol and Dodecylphenol-9 mole ethoxylate; and mixtures thereof.

Other crystallization initiators which are useful in the present invention include ethoxylated nonylphenol, ethoxylated octylphenol, ethoxylated aliphatic alcohols having between 10 and 20 carbon atoms, such as the surfactants Brij and Tween, and mixtures thereof.

Still other crystallization initiators which are useful in the present invention include polyethylene glycol; polymers and copolymers of ethylene oxide and propylene oxide having a molecular weight between approximately 1,000 and 15,000, such as Pluronic P-65 and Genapol PF-80, sodium salts of modified lignin sulfonate, such as Reax 80C; polyoxyethylene cetyl ether; sodium polyacrylate; sorbitan tristearate; dimethyl octyndiol; diamyl ester of sodium sulfosuccinic acid; ethoxylated castor oil; amine salt of dodecylbenzene sulfonic acid; glycerol monostearate; glycerol distearate; stearic acid; glycol monolaurate; disodium salt of N-tallow beta iminodipropionate; finely divided clay, such as kaolin and bentonite; modified clay, such as Bentone and Attasorb; finely divided silicas, such as Silica FK 300DS and Sipernat 50S; modified silicas, such as Sipernat D10 and Aerosil R812; microcrystalline cellulose; polyoxyethylene stearyl ether; ethoxylated dinonylphenol; trihexadecylamine; modified methylpyridinium chloride, such as Emcol E-607 and Emcol E-607S; ethoxylated sodium lauryl alcohol sulfate; dibenzidine sorbitol; ditolylidene sorbitol; dodecylbenzene sulfonic acid; sodium naphthylenesulfonic acid formaldehyde copolymers, such as Daxad 15 and Daxad 21; tall oil fatty amides, such as Witcamide 511 and Witcamide 512; and mixtures thereof. The crystallization initiators can be added to the aqueous phase prior to emulsification of the pendimethalin therein. Alternately, the crystallization initiators can be added to the molten pendimethalin before emulsification in the aqueous phase. The amount of the crystallization initiator which is added to the aqueous phase or molten active material is that amount which is effective to promote the solidification of the pendimethalin in the microcapsule at ambient temperatures, generally between approximately 0.1% and 10% by weight; preferably, between approximately 0.5% and 2% by weight.

Generally speaking, crystallization initiators useful in the present invention are those materials which are soluble in molten pendimethalin, i.e., pendimethalin at temperatures above 60° C., up to approximately 5% by weight, preferably 1% by weight, and which cause the pendimethalin to substantially solidify upon cooling to ambient temperatures, e.g., 20° C. to 25° C. The crystallization initiating compounds useful in the present invention also must not substantially interfer with the properties of the film forming compounds with respect to their ability to encapsulate the pendimethalin.

With the use of the crystallization initiators of the present invention, the pendimethalin after it has been microencapsulated can be repeatedly temperature cycled through the pendimethalin's melting point and upon cooling to ambient or room temperature will return to the solid form. Such conditions of temperature cycling are often found under typical storage conditions. Therefore, it has been unexpectedly discovered that the use of the crystallization initiators of the present invention makes the microencapsulated pendimethalin more storage stable.

Proper packaging of the spray-dried encapsulated active material provides important benefits. In general, any package, such as bottles, jugs, bags, and the like may be used as long as a sufficient moisture barrier is obtained, to prevent caking of the product due to absorption of moisture from the air on storage. Surprisingly, pendimethalin in the spray-dried product prepared and/or packaged by the above method can be stored at temperatures above its melting point without harming its physical properties after it returns to ambient temperatures. Accordingly, the composition of the present invention has the property of improved storage stability.

The microencapsulated pendimethalin in accordance with the present invention is a dry, free flowing powdery substance. The microencapsulated pendimethalin can be readily wetted and dispersed in water to form a sprayable composition. When the microencapsulated pendimethalin is added to water, the water-soluble, film-forming polymer which forms the wall of the microcapsule readily dissolves. The result is an aqueous dispersion of pendimethalin. The dispersion or suspension of pendimethalin in accordance with the present invention has improved properties of suspensibility, i.e., less material will settle out of the dispersion for a given amount of time than prior art compositions. The aqueous dispersion of pendimethalin can then be used in a conventional manner, such as by spraying an area to be treated.

The following examples are illustrative of the present invention and are not intended to limit the scope of the invention as set forth in the appended claims. All temperatures are in degrees Celsius and all percentages are by weight unless otherwise stated. Some of the examples below are described using crystallization initiating materials designated by their tradename. Table 1 lists the tradename of some of those materials and their corresponding common name.

TABLE 1

| Tradename | Common Name |
|---|---|
| Atlox 847 | Polyethoxylated ester |
| Brij 52 | Polyoxyethyleneated cetyl alcohol (2 moles EO) |
| Myrij 45 | Polyoxyethlenated stearic acid (8 moles EO) |
| Plurafac B-26 | Ethoxylated propoxylated C12-C18 alcohols |
| Tween 60 | Polyoxyethlyenated sorbitan monostearate (20 moles EO) |
| Iconol NP-100 | Polyoxyethylenated nonylphenol (100 moles EO) |
| Igepal CO-630 | Polyoxyethylenated nonylphenol (9 moles EO) |
| T-Det DD7 | Polyoxyethyleneated dodecylphenol (7 moles EO) |
| Triton X-114 | Polyoxyethyleneated octylphenol (7-8 moles EO) |
| Span 60 | Sorbitan monostearate |
| Span 80 | Sorbitan monooleate |
| Surfonyl 104 | 2,4,7,-tetramethyl-5-decyne-4,7-diol |
| Surfonyl SE | 2,4,7,9-tetramethyl-5-decyn-4,7-diol mixture |
| Genapol PF-80 | Ethylene oxide-propylene oxide copolymer |
| Pluronic F-38 | Polyoxypropylene glycol (mo. wt. 950 + 85 moles EO) |
| Pluronic P-65 | Polyoxypropylene glycol (mol. wt. 1750 + 40 moles EO) |
| Pluronic 10R-5 | Polyoxypropylene glycol (mol. wt. 1000 + 50% EO) |
| Pluronic 25R-2 | Polyoxypropylene glycol (mol. wt. 2500 + 20% EO) |
| Sellogen HR | Sodium diisopropyl naphthalene sulfonate |

TABLE 1-continued

| Tradename | Common Name |
|---|---|
| Triton X-180 | Blend of alkyl polyether alcohol with organic sulfonates |
| Toximul MP-10 | Sulfonate/nonionic blend |
| Gafac LO-529 | Sodium salt of complex organic phosphate ester |
| Gafac RS-610 | Poly(oxy-1,2-ethanediyl), alpha-tridecyl-omega-hydroxy phosphate |
| Nekal WT-27 | Sodium dioctylsulfosuccinate |
| Pluronic E-1450 | Polyethylene glycol 1450 mol. wt. |
| Pluronic E-4000 | Polyethylene glycol 4000 mol. wt. |
| Reax 80C | Sodium lignosulfate (2–2.5 moles sulfonate per 1000 g low mol. wt. lignin |
| Daxad 30-30 | Sodium polyacrylate solution |
| Sokalan PA-15 | Sodium salt of polyacrylic acid, 1200 mol. wt. |
| Sokalan PA-75 | Sodium salt of polyacrylic acid, 75,000 mol. wt. |
| Volclay 325 | Sodium bentonite |
| Polargel T | Purified bentonite |
| Flogard SP | Silicon dioxide |
| Sipernat D17 | Silicon dioxide |
| Hubersorb 600 | Calcium silicate |
| Avicel NF | Microcrystalline cellulose |
| Millad 3905 | Dibenzylidine sorbitol |
| Millad 3940 | Bis-O-((4-methlyphenyl)methlyene)-D-glucitol |

EXAMPLE 1

7,000 g. of water are heated and maintained at 60° C. To this is slowly added 726.6 g. of partially hydrolyzed polyvinyl alcohol (PVA) with a degree of hydrolysis of 87–89% and a molecular weight of 10,000–30,000. The mixture is agitated until the PVA is completely dissolved. To this aqueous solution is then added 22.5 g. of sodium dioctyl sulfosuccinate. Further stirring is carried out, with the temperature of the solution being maintained at 65° C. Then, 2,250.9 g. of technical grade pendimethalin (N-( 1-ethylpropyl)-3,4-dimethyl-2,6-dinitrobenzenamine) is melted by heating to 70° C., is added to the aqueous solution and emulsified with a high shear homogenizer. The emulsion particle size is further reduced by passing the emulsion through a pressure valve homogenizer until an average size of 4 microns is achieved. The emulsion is then spray dried at an inlet air temperature of 190° C., and an outlet air temperature of 105° C. A laboratory type spray dryer is used with two fluid nozzle atomization.

1,345 g. of a dry free-flowing powder is obtained with a particle size of 30–70 microns. The product is then packaged in foil laminate bags. The product exhibits excellent properties on dilution in water, wetting almost instantly, producing a stable suspension on standing.

The finished product contains 70% by weight of pendimethalin and maintains its biological and physical properties on storage at both ambient and elevated temperatures.

EXAMPLE 2

3,500 g. of water are heated to 60° C. and, under moderate agitation, 363.3 g. of partially hydrolyzed polyvinyl alcohol, having a degree of hydrolysis of 87%–89% and a molecular weight of 10,000–30,000 is added. To this aqueous solution is then added 11.2 g. of sodium dodecylbenzene sulfonate and stirring continues. 1,125.4 g. of technical grade pendimethalin [N-(1-ethylpropyl)-3,4-dimethyl-2,6 -dinitrobenzenamine] is melted by heating to 60° C. The molten technical material is added to the polymer solution and agitated with a high shear homogenizer until a uniform dispersion is obtained. A pressure valve homogenizer is then used to reduce the droplet particle size to 4 microns.

The emulsion thus formed is spray dried, using a laboratory spray dryer fitted with a two-fluid nozzle atomizer, at an inlet air temperature of 180° C., and an outlet air temperature of 106° C. A free-flowing powder is obtained with a particle size of 30–70 microns.

The finished product contains 70% by weight of pendimethalin and maintains its physical properties on storage at both ambient and elevated temperatures. The product has excellent properties on dilution with water, wetting rapidly to produce a stable suspension on standing.

EXAMPLE 3

The same process as described above in Example 2 is followed except the PVA has an average molecular weight of approximately 40,000.

EXAMPLE 4

2,250 g. of water are heated to 60° C. and stirred while 11.25 g. of tetramethyl decyn-diol and 363.3 g. of 87–89% hydrolyzed polyvinyl alcohol (molecular weight 10,000–30,000) are added and dissolved. 1125.4 g. of molten pendimethalin are then added with high shear to produce an emulsion. The emulsion particle size is further reduced by passing the emulsion through a pressure valve homogenizer to produce an emulsion particle size of 2.6 microns.

The emulsion is then spray dried at an inlet air temperature of 188° C. and an outlet air temperature of 107° C., yielding 596 g. of a free-flowing powder with a particle size between 30 and 70 microns. The powder produced by the spray dryer is then introduced into a fluidized bed and cooled at a temperature of 20° C.

EXAMPLE 5

557.1 g. of water are heated to 60° C. and stirred while 49.4 g. of 87–89% hydrolyzed polyvinyl alcohol (molecular weight 10,000–30,000) are slowly added. When the PVA is completely dissolved, 0.3 g. of sodium dioctyl sulfosuccinate is added.

Separately, 240.0 g. of pendimethalin are melted and held at 60° C. with stirring while 0.3 g. of 3-hydroxy benzoic acid is added and dissolved. This solution is then added to the PVA solution and emulsified with a high shear homogenizer to produce an emulsion particle size of 4 microns.

The emulsion is then spray dried in a laboratory type spray dryer at an air inlet temperature of 187° C. and air outlet temperature of 105° C. using two-fluid nozzle atomization. 49.3 g. of a free flowing powder are produced with a particle size of 15–30 microns.

EXAMPLE 6

The procedure of Example 1 is followed except the following water-soluble, film forming polymers are separately substituted for the polyvinyl alcohol:
A. Sodium Carboxymethylcellulose
B. Gum Acacia
C. Poly (Acrylic Acid)
D. Casein
E. Hydrolyzed Maltodextrin (5 Dextrose equivalent)
F. Modified starch
G. Starch
H. Polyacrylamide
I. Hydroxyethylcellulose
J. Polyvinylpyrrolidone.

The products of the spray drying process are dry free-flowing powders of pendimethalin microencapsulated in the above-referenced polymers.

EXAMPLE 7

The procedure of Example 1 is followed except that the crystallization initiators listed in Table 2 below are separately substituted for the sodium dioctyl sulfosuccinate:

TABLE 2

| Crystallization Initiator | Example |
| --- | --- |
| A. organic acids and salts | Benzoic acid |
| | Sodium Benzoate |
| | Salicylic acid |
| | Hydroxybenzoic acid |
| | Palmitic acid |
| | Stearic acid |
| B. Dinitroanilines | 3,5-dinitro-$N^4$,$N^4$-dipropylsulfanilimide |
| | 2-dipropyl-3,5-dinitrobenzotrifluoride |
| C. Ethoxylated polyester surfactants | Atlox 847 |
| D. Ethoxylated alcohols and esters | Brij 52 |
| | Myrj 45 |
| | Plurafac B-26 |
| E. Ethoxylated alkylphenols | Iconol NP-100 |
| | Igepal CO-630 |
| | T-Det DD7 |
| | Triton X-114 |
| F. Sorbitan esters | Span 60 |
| | Span 80 |
| | Tween 60 |
| G. Acetylenic diols | Surfonyl 104 |
| | Surfonyl SE |
| H. Block copolymers of alkylene oxides | Genapol PF-80 |
| | Pluronic F-38 |
| | Pluronic P-65 |
| | Pluronic 10R |
| | Pluronic 25R-2 |
| I. Alkylaryl sulfonates | Calcium dodecylbenzenesulfonate |
| | Sellogen HR |
| | Triton X-180 |
| | Toximul MP-10 |
| J. Organic phosphate esters | Gafac LO-529 |
| | Gafac RS-610 |
| K. Sulfonated aliphatic polyesters | Nekal WT-27 |

The spray drying process produces a free flowing powder containing microencapsulated solidified pendimethalin.

EXAMPLE 8

The procedure of Example 1 is followed except that the crystallization initiators listed in Table 3 below are separately substituted for the sodium dodecylbenzene sulfonate:

TABLE 3

| Crystallization Initiator | Example |
| --- | --- |
| A. Polyethylene glycol | Pluronic E-1450 |
| | Pluronic E-4000 |
| B. Sodium salts of modified sulfonate | Reax 80C |
| C. Sodium polyacrylates | Daxad 30-30 |
| | Sokalan PA-15 |
| | Sokalan PA-75 |
| D. Glycerol esters | Glycerol monooleate |
| E. Finely divided clays | Volclay 325 |
| | Kaolin |
| | Polargel T |
| F. Silicas and modified silicas | FloGard SP |
| | Sipernat D17 |
| | Hubersorb 600 |
| | Avicel NF |

TABLE 3-continued

| Crystallization Initiator | Example |
| --- | --- |
| G. Micorcrystalline cellulose | Avicel NF |
| H. Sulfur | |
| I. Hydrocarbons | Paraffin wax |
| | Hexatriacontane |
| J. Straight chain alcohols | Stearyl alcohol |
| | Cetyl alcohol |
| K. Substituted sorbitols | Millad 3905 |
| | Millad 3940 |

The products of the spray drying are dry free flowing powders containing microencapsulated solidified pendimethalin.

EXAMPLE 9

A spray drier feed emulsion of pendimethalin is prepared using the formulation of Example 2. The feedstock emulsion is spray dried in a tall-form tower using hydraulic atomization. Spray drying conditions are 235° C. inlet air temperature and 106° C. outlet air temperature. The feed atomization pressure is 940 p.s.i.

The free flowing product obtained is transferred to a vibrating fluid bed to quickly cool the product to ambient temperatures. The inlet air to the fluid bed is maintained at 20° C. Additional material is collected from the spray drier and packaged without fluid bed cooling.

Samples of both products are placed in storage under various storage conditions, i.e., at 25° C., 37° C. and 50° C., and under a cycled temperature program where the storage temperature is cycled between 25° C. and 60° C. with 24 hours storage at each temperature. At intervals, the products are sampled and analyzed for wetting, dispersion properties, redispersion, suspensibility, percent crystallinity and wet sieve retention.

In the following tables, i.e., Tables 4–6, wetting time is given in seconds for a measured amount of the product to wet and fall below the surface of a beaker of water (a shorter wetting time relating to better product quality. The dispersion is given in inversions of a graduated cylinder to obtain a uniform suspension of the product in water (fewer inversions relating to better product quality). Redispersion is the number of inversions of the cylinder required to completely resuspend the product after standing 30 minutes (fewer inversions relating to better product quality). Crystallinity is the percentage of pendimethalin in a solid, crystalline form as measured by differential scanning calorimetry. Wet sieve retention is the percent of undispersed material remaining on 50 and 100 mesh sieves after washing the sieves with water (a lower percentage retention relating to better product quality).

For comparison, a sample of conventionally prepared granular pendimethalin is included in the storage stability testing. This product contains 60% pendimethalin and consists of small pellets 1–3 mm in diameter.

TABLE 4

SPRAY DRIED PENDIMETHALIN PRODUCT - FLUID BED COOLED

| Storage Cond. | Storage Time | Wet Time | Disp | Redisp. | Susp. | Crystal. | Wet Sieve. 50 mesh | 100 mesh |
|---|---|---|---|---|---|---|---|---|
| Ambient | 8 weeks | 1 | 4 | 2 | 100 | 83 | 0 | 0 |
| 37° C. | 8 weeks | 1 | 5 | 3 | 99 | 88 | 0 | 0 |
| 50° C. | 8 weeks | 1 | 3 | 2 | 100 | 80 | 0 | 0 |
| Cycled | 8 weeks | 1 | 3 | 2 | 100 | 80 | 0 | 0 |

TABLE 5

SPRAY DRIED PENDIMETHALIN PRODUCT - NOT FLUID BED COOLED

| Storage Cond. | Storage Time | Wet Time | Disp | Redisp. | Susp. | Crystal. | Wet Sieve. 50 mesh | 100 mesh |
|---|---|---|---|---|---|---|---|---|
| Ambient | 8 weeks | 4 | 5 | 3 | 84 | 74 | 0 | 0 |
| 37° C. | 8 weeks | 4 | 7 | 2 | 78 | 78 | 0 | 0 |
| 50° C. | 8 weeks | 7 | 8 | 2 | 88 | 76 | 0 | 0 |
| Cycled | 8 weeks | 2 | 8 | 2 | 100 | 63 | 0 | 0 |

TABLE 6

CONVENTIONAL GRANULATED PENDIMETHALIN

| Storage Cond. | Storage Time | Wet Time | Disp | Redisp. | Susp. | Crystal. | Wet Sieve. 50 mesh | 100 mesh |
|---|---|---|---|---|---|---|---|---|
| Ambient | 8 weeks | 2 | 15 | 2 | 57 | 95 | 0 | 0 |
| 37° C. | 8 weeks | 2 | 20 | 2 | 53 | 97 | 0 | 0 |
| 50° C. | 8 weeks | 1 | 20 | 2 | 47 | 85 | 0 | 0.3 |
| Cycled | 8 weeks | 1 | >60 | >60 | 15 | 99 | 98 | 0 |

The foregoing data clearly shows that the microencapsulated form of pendimethalin in accordance with the present invention possesses improved properties compared to conventional commercial pendimethalin products. The advantages of the microencapsulated form of pendimethalin over the conventional granular formulation of pendimethalin are most evident in the greatly improved dispersibility, suspensibility and wet sieve properties. The storage stability of the microencapsulated form of pendimethalin is likewise enhanced, particularly under conditions of cycled storage at temperatures above the melting point of pendimethalin.

The foregoing description relates to certain embodiments of the present invention, and modifications or alterations may be made therein without departing from the spirit and scope of the invention as defined in the following claims.

I claim:

1. A storage stable pesticidal composition having improved properties of wetting and dispersion, said composition comprising pendimethalin and a crystallization initiating compound microencapsulated in a microcapsule of a water-soluble, film-forming polymer, said crystallization initiator being present in an amount sufficient to enhance solidification of said pendimethalin in said microcapsule and to thereby improve the properties of wetting and dispersion of said composition.

2. The pesticidal composition of claim 1, further comprising an effective amount of a crystallization initiating compound selected from the group consisting of benzoic acid; sodium benzoate; salicylic acid; 3-hydroxybenzoic acid; 4-hydroxybenzoic acid; 3, 5-dinitro-$N^4$, $N^4$-dipropyl-sulfanilamide; 2-dipropylamino- 3, 5-dinitrobenzotrifluroride, sodium dodecylbenzene sulfonate; calcium dodecylbenzene sulfonate; tetrasodium N-(1, 2 -dicarboxyethyl)-N-octadecylsulfosuccinamate; dioctyl ester of sodium sulfosuccinic acid; sodium N-methyl-N-oleoyl taurate; sorbitan monolaurate; tetramethyl decyndiol; dodecylphenol-9 mole ethoxylate; polyoxyethylene (20) sorbitan monostearate; polyoxyethylene (20) sorbitan trioleate; diethylene glycol monostearate; polyethylene glycol 400 monostearate, sorbitan monostearate; sorbitan monooleate; sorbitan trioleate; polyoxyethylene (20) sorbitan monolaurate; polyoxyethylene (20) sorbitan monooleate; nonylphenol 4 mole ethoxylate and mixtures thereof.

3. The pesticidal composition of claim 1, further comprising an effective amount of a crystallization initiating compound selected from the group consisting of ethoxylated nonylphenol, ethoxylated octylphenol, ethoxylated aliphatic alcohols having between 10 and 20 carbon atoms, and mixtures thereof.

4. The pesticidal composition of claim 1, further comprising an effective amount of a crystallization initiating compound selected from the group consisting of polyethylene glycol; polymers and copolymers of ethylene oxide and propylene oxide having a molecular weight of between approximately 1,000 and 15,000 ; sodium salts of modified sulfonate lignin; polyoxyethylene cetyl ether; sodium polyacrylate; sorbitan tristearate; dimethyl octyndiol; diamyl ester of sodium sulfosuccinic acid; ethoxylated castor oil; amine salt of dodecylbenzene sulfonic acid; glycerol monostearate; glycerol distearate; stearic acid; glycol monolaurate; disodium salt of N-tallow beta iminodipropionate; finely divided clay; finely divided silicas; microcrystalline cellulose; polyoxyethylene stearyl ether; ethoxylated dinonylphenol; trihexadecylamine; methylpyridinium chloride; ethoxylated sodium lauryl alcohol sulfate; dibenzidine sorbitol; ditolylidene sorbitol; dodecylbenzene sulfonic acid; sodium naphthylenesulfonic acid formaldehyde copolymers; tall oil fatty amides; and mixtures thereof.

5. The pesticidal composition of claim 1, wherein said water-soluble film forming polymer is selected from the group consisting of polyvinyl alcohol, polyvinylpyrrolidone, starches, modified starches, alginates, hydroxyalkylcellulose, hydroxyalkylcellulose derivatives, poly (acrylic acid), polyacrylamide, natural gums, dextrins and proteins.

6. The pesticidal composition of claim 1, wherein said water-soluble film forming polymer is selected from the group consisting of polyvinyl alcohol, polyvinylpyrrolidone, hydroxyalkylcellulose, gum arabic, gelatin and casein.

7. The pesticidal composition of claim 1, wherein said pendimethalin comprises between approximately 60% and 75% by weight of said composition.

8. The pesticidal composition of claim 1, wherein said water-soluble film forming agent comprises between approximately 15% and 40% by weight of said composition.

9. The pesticidal composition of claim 1, wherein said crystallization initiating compound comprises between approximately 0.5% and 1.25% by weight of said composition.

10. The pesticidal composition of claim 1, wherein said crystallization initiating compound comprises between approximately 0.5% and 1.25% by weight of said composition.

11. The pesticidal composition of claim 1, wherein said crystallization initiating compound comprises between approximately 0.5% and1.25% by weight of said composition.

12. A pesticidal composition having improved properties of wetting and dispersion, said composition comprising between approximately (60% and 75% by weight pendimethalin, between approximately 0.5% and 1.25% by weight sodium dodecylbenzene sulfonate and between approximately 15% and 40% by weight polyvinyl alcohol, wherein said pendimethalin and said sodium dodecylbenzene sulfonate are incorporated in a microcapsule of polyvinyl alcohol.

13. A method of using a pesticidal composition having improved properties of wetting and dispersion comprising the steps of:

combining with water a pesticidally effective mount of a composition comprising pendimethalin and a crystallization initiating compound microencapsulated in a water-soluble, film forming polymer, said crystallization initiator being present in an amount sufficient to enhance solidification of said pendimethalin in said microcapsule and to thereby improve the properties of wetting and dispersion of said composition, whereby said microcapsule dissolves in said water thereby providing an aqueous dispersion of pendimethalin; and applying said aqueous dispersion of pendimethalin to an area to be treated.

\* \* \* \* \*

UNITED STATES PATENT AND TRADEMARK OFFICE
CERTIFICATE OF CORRECTION

PATENT NO. : 5,461,027

DATED : October 24, 1995

INVENTOR(S) : Elliot Bergman

It is certified that error appears in the above-identified patent and that said Letters Patent is hereby corrected as shown below:

Cover page, item [75], after "Inventor:"

Change "Elliot Bergman, Valdosta, Ga." to --

John Misselbrook, Lawrenceville, N.J.; Edwin F. Hoff Jr., Elliot Bergman, both of Valdosta, Ga; Larry J. McKinney, Hahira, Ga; James H. LeFiles, Valdosta, Ga.--

Signed and Sealed this

Eleventh Day of March, 1997

Attest:

BRUCE LEHMAN

Attesting Officer

Commissioner of Patents and Trademarks